United States Patent [19]

Muhler et al.

[11] 4,428,928

[45] Jan. 31, 1984

[54] DENTIFRICE PREPARATIONS COMPRISING CALCINED KAOLIN ABRASIVES

[75] Inventors: Joseph C. Muhler, Howe; Mark S. Putt, Fort Wayne, both of Ind.

[73] Assignee: Indiana University Foundation, Bloomington, Ind.

[21] Appl. No.: 393,046

[22] Filed: Jun. 28, 1982

[51] Int. Cl.$^3$ .......................... A61K 7/16; A61K 7/18
[52] U.S. Cl. .......................................... 424/49; 424/52
[58] Field of Search .................................... 424/49–58

[56] References Cited

U.S. PATENT DOCUMENTS

| | | | |
|---|---|---|---|
| 3,105,013 | 9/1963 | Saul et al. | 424/49 |
| 3,282,792 | 11/1966 | Fiscella | 424/49 |
| 3,450,813 | 6/1969 | Muhler | 424/49 |
| 4,108,981 | 8/1978 | Muhler et al. | 424/49 |
| 4,122,163 | 10/1978 | Muhler et al. | 424/49 |

FOREIGN PATENT DOCUMENTS 49-24224  6/1974  Japan .

*Primary Examiner*—Shep K. Rose
*Attorney, Agent, or Firm*—Kirkland & Ellis

[57] ABSTRACT

Incorporation of talc in dentifrice preparations based on calcined kaolins enhances the rheological properties of such dentifrices. In addition, new and more effective dentifrice preparations may be obtained by employing therein a cleaning and polishing constituent comprising a mixture of calcined kaolin, talc and titanium dioxide. Additionally, anticariogenic adjuvants, such as sodium fluoride and stannous fluoride, especially a 1:2 molar mixture thereof, may be incorporated in such dentifrice preparations.

1 Claim, 4 Drawing Figures

DENTIFRICE PREPARATIONS COMPRISING CALCINED KAOLIN ABRASIVES

BACKGROUND OF THE INVENTION

1. Field of the Invention

The present invention relates to new dentifrice cleaning and polishing agents and to the formulation and utilization of dentifrice preparations incorporating such cleaning and polishing agents. In particular, the invention relates to a dentifrice cleaning and polishing composition comprising calcined kaolin in combination with talc and preferably titanium dioxide.

Incorporation of talc into a calcined kaolin based dentifrice permits the rheological properties of the dentifrice to be significantly improved. The provision of a talc modifier also enhances the polishing ability of calcined kaolins, improves fluoride and stannous ion availability and reduces abrasion. Moreover, the addition of titanium dioxide permits these advantages to be achieved without sacrificing the desired whiteness of the dentifrice.

The compositions of this invention serve to clean and polish dental hard tissue in a novel manner such that reaccumulations of pellicle and materia alba and occurrence and reformation of plaque and calculus on oral hard tissue are markedly reduced, thereby significantly reducing the occurrence of gingivitis and other soft tissue and periodontal disease. Fluoride-containing anticariogenic adjuvants such as sodium fluoride, stannous fluoride, and, especially, 1:2 molar mixtures thereof, may also usefully be incorporated in such compositions.

2. Description of the Prior Art

Dental research has developed substantial evidence that beyond the age of thirty-five years loss of teeth is predominantly the result of periodontal involvement rather than dental caries. However, evidence in the literature suggests that gingivitis itself may be present in a large portion of the population at a much earlier age. In this form the disease is reversible. A major factor contributing to periodontal disease is the accumulation of certain forms of dental plaque and calculus (e.g., salivary tartar) on the teeth. These accumulations result in tissue inflammation of the surrounding gingiva, and, as the condition increases in severity, the peridontal fibers and supporting bone subsequently become affected. These reactions lead to the destruction of the supporting structures and the subsequent mass loss, in most instances, of sound teeth.

Heretofore, commercially available dentifrices containing abrasives such as insoluble sodium metaphosphate ($NaPO_3$), calcium hydrogen phosphate dihydrate/anhydrous calcium hydrogen phosphate, ($CaHPO_4.2H_2O/CaHPO_4$), calcium pyrophosphate ($Ca_2P_2O_7$), and silica ($SiO_2$) have exhibited relatively unsatisfactory enamel-polishing qualities and consequently have not been wholly effective in preventing the reaccumulation of materia alba, oral debris, plaque, pellicle, exogenous stains, and dental calculus. In particular, while conventional cleaning and polishing agents used with a toothbrush are capable, to varying degrees, of removing materia alba, food particles, exogenous stains, and other tooth surface pigmentations when utilized in ordinary daily brushings, they have not exhibited the ability to remove the more resistant forms of enamel pigments and to produce a smooth tooth surface resistant to dental plaque and calculus formation. Furthermore, these conventional abrasives leave the teeth esthetically less desirable than would more effective polishing agents.

The beneficial effects, in terms of a reduction in the incidence of dental caries, resulting from the incorporation of water-soluble fluoride salts are well known. However, efforts to utilize such salts in dentifrices suitable for home use have been handicapped by the tendency for fluoride ions to be deactivated and rendered unavailable by other ingredients, particularly the abrasive component of such dentifrices. While generally speaking, dentifrice abrasives in therapeutic products used today are to varying degrees compatible with fluoride agents, there is a wide variation in compatibility. Calcium-containing abrasives are not particularly compatible. While the non-calcium-containing abrasives are somewhat more compatible, they frequently are inferior with regard to enamel polishing.

Saul et al., U.S. Pat. No. 3,105,013 recommends using calcined aluminum silicate as a dental abrasive on the basis of its compatibility with fluoride adjuvants. However, the preferred material of Saul et al. is commercially available under the trademark "Kaopolite SF". Kaopolite SF is off-white in color and is thus esthetically undesirable in a commercial dentifrice.

Japanese Pat. No. 24224/74 describes dental abrasives combining calcined kaolins with other abrasives such as calcium carbonate, calcium hydrogen phosphate dihydrate, and the like.

Applicants' U.S. Pat. No. 4,122,163 describes dentifrices formulated with highly purified calcined kaolin particles from which titanium impurities have been excluded. The patent also describes replacement of the kaolin with other dental abrasive materials including talc, but it does not recognize that the rheological properties of calcined kaolin may be improved thereby or the kaolin need not be specially purified in order to be successfully employed, nor does it disclose that the overall performance of the abrasive can in fact be improved.

The prior art calcined kaolin dentifrices have all encountered formulation problems due to the dilatancy of the material when provided in paste form. In addition, they encounter shelf life problems when used with certain anticariogenic additives.

Thus, prior art materials intended for use as cleaning and polishing constituents of dentifrice preparations have not been entirely satisfactory in one or more of the following respects: relatively poor cleaning and polishing performances (especially with respect to prevention of reaccumulation of dental calculus, pellicle, materia alba, and the more resistant forms of oral hard tissue stains and pigmentations); incompatibility with fluoride and stannous ion-containing anticariogenic agents; adverse abrasion; difficult, expensive manufacturing requirements; and rinsing and rheological problems.

SUMMARY OF THE INVENTION

In accordance with the present invention, it has been found that new and more effective dentifrice preparations overcoming the foregoing disadvantages may be obtained by incorporating therein as cleaning and polishing constituents a mixture of calcined kaolin, talc, and titanium dioxide. More particularly, the mixture comprises at least about 20% calcined kaolin; at least about 10% talc, and about 2-20% titanium dioxide, all by weight of the mixture. The particles are predominantly less than about 10 microns in diameter, and the mixture when formulated into a dentifrice has a whiteness score of at least about 79%.

It has been further found that the novel cleaning and polishing agents of the present invention may be used with non-toxic amounts of water-soluble anticariogenic adjuvants such as sodium fluoride or stannous fluoride. It is especially preferred to employ a 1:2 molar mixture of sodium fluoride and stannous fluoride.

It has likewise been discovered that the regular application of the dentifrice preparation of the present invention to the teeth provides a novel method for cleaning and polishing teeth and for reducing the incidence of gingival disease.

The method aspects of this invention further involve the discovery that the rheological properties of a dentifrice preparation comprising calcined kaolin as a cleaning and polishing agent may be improved by incorporation with the calcined kaolin at least about 10% talc by weight of the cleaning and polishing agent.

Through the use of the cleaning and polishing agents of the present invention the difficulties experienced with prior art dentifrice cleaning and polishing agents may be overcome, and compositions of the present invention may therefore be used to formulate dentifrices with superior cleaning and polishing capabilities, with enhanced anticariogenic agent compatibilities, greater fluoride uptake by the dental enamel, and with improved rheological properties.

Accordingly, it is a primary object of the present invention to provide a cleaning and polishing agent which is capable of reducing the reformation of dental calculus and the incidence of gingivitis and yet which is suitable for incorporation in a dentifrice preparation.

Another object of the present invention is to provide an anticalculus cleaning and polishing agent of the character described which is effective in removing pellicle and dental enamel stains and pigmentations.

Another object of the present invention is to provide anticalculus dentifrice preparations incorporating a cleaning and polishing agent of the character described.

A still further object is to provide a dentifrice preparation incorporating at least one fluoride-containing anticariogenic adjuvant in combination with an anticalculus cleaning and polishing agent of the character described which further serves to enhance the effectiveness of the anticariogenic adjuvant.

DESCRIPTION OF THE PREFERRED EMBODIMENTS

Figure 1:
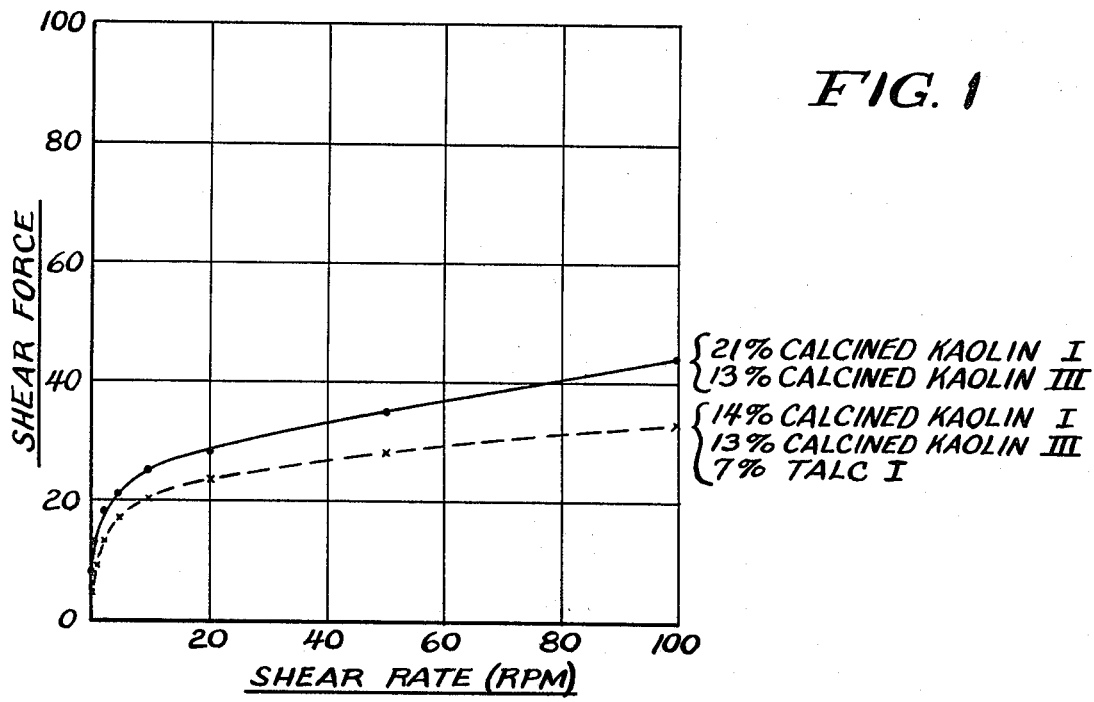
FIGS. 1-4 are graphs plotting shear force versus shear rate for four series of paired experimental dentifrices demonstrating the improvement of calcined kaolin dentifrices containing talc formulation modifiers.

In accordance with the subject invention, it has been discovered that the rheological properties such as shear thinning and dilatancy of calcined kaolin dentifrices are improved substantially by incorporating talc therewith. Shear thinning is especially important in that it improves the efficiency of tube filling during packaging and the extrudability and dispersibility during use by the consumer. Improvement in rinsibility has also been noted.

It has also been found that optimal cleaning and polishing characteristics for a dentifrice cleaning and polishing agent are exhibited by a mixture of calcined kaolin, talc as an abrasive and formulation modifier, and titanium dioxide as a whitener and polishing enhancer. The mixture particles are at least predominantly (i.e., 50% or more by weight) less than about 10 microns in diameter, and the mixture when formulated into a dentifrice has a whiteness score of at least 79%. Whiteness as used herein is determined in accordance with the procedure described hereinafter in detail using a wave-length of 450 nanometers.

In addition, it has been found that the cleaning and polishing agent mixture may be advantageously used with water-soluble fluoride-ion-containing anticariogenic adjuvants such as sodium fluoride, NaF, stannous fluoride, $SnF_2$, or, preferably, a 1:2 molar mixture thereof.

As a result of the foregoing, the cleaning and polishing compositions of the present invention find utility in therapeutic dentifrices (i.e., dentifrices containing at least one anticariogenic ionic adjuvant in combination with a compatible cleaning and polishing agent and designed to reduce the incidence and severity of dental caries) or dentifrices which, although not containing fluorides or other anticariogenic agents, nonetheless have therapeutic utility in reducing gingival disease.

CLEANING AND POLISHING AGENTS

The calcined kaolin employed in accordance with this invention may be obtained by calcining (i.e., heat treating) kaolinite, $[Al_4Si_4O_{10}(OH)_8]$, which has been mined, cleaned, dried and fractionated. Prior to calcining, the material may, but need not, be subjected to purification procedures involving magnetic separations or the flocculation and related steps described in U.S. Pat. No. 3,477,809 in order to remove impurities.

The purified material is calcined at a temperature lying in the range of about 950° C. to 1150° C. If the temperature does not reach 950° C., the purified kaolinite remains predominantly meta-kaolin, a material which is insufficiently hard to clean and polish satisfactorily from a dental standpoint. Material which has been calcined at about 950° C. is predominantly gamma alumina generally taking the form of spinel-type crystals. However, if the purified material is more highly calcined, (i.e., is subjected to temperatures of up to about 1150° C.), the gamma alumina undergoes a change to highly crystalline mullite ($3Al_2O_3.2SiO_2$), generally taking the form of small, needle-like crystals. If the materials are overcalcined (i.e., subjected to temperatures of about 1250° C. or more), larger mullite crystals and materials such as cristobolite ($SiO_2$) are formed. Material containing large amounts of cristobolite and large mullite crystals are unsatisfactory from a dental standpoint because of their tendency to scratch the tooth enamel unless reduced in size by milling or grinding. As a consequence, the purified, calcined kaolins used in accordance with this invention are desirably predominantly of the gamma alumina and/or mullite form.

After calcining, in which the material agglomerates into large masses, grinding and/or milling must be used to obtain an abrasive having a particle size distribution lying in the range found to be useful in dentifrice preparations.

When lower calcining temperatures are employed (i.e., in the range of about 950° C. to 1050° C.), more economical dry grinding processes such as conventional Bauer-milling, may be employed. However, where higher calcining temperatures of 1050° C. and especially about 1150° C. are employed, it has been found that the relatively greater amounts of hard crystalline material formed at these temperatures may most conveniently be treated by using known wet-sand grinding procedures. Sand grinding techniques may be employed with all of the abrasives of this invention although, as noted, for reasons of economy, it is preferred to use Bauer-milling treatments for materials calcined in the lower temperature ranges. Bauer-milling procedures may be employed with materials calcined in the range of about 1150° C., but it is preferred to use sand grinding techniques with these materials.

Properties of several typical calcined kaolins that may be used in accordance with this invention are given in Table I.

TABLE I

| CALCINED KAOLIN PROPERTIES | | | |
|---|---|---|---|
| | Sample I | Sample II | Sample III |
| Physical Properties | | | |
| Median Particle Size (micrometers) | 1.8 | 0.7 | 1.4 |
| Particle Size (% <2 micrometers) | 56 | 82 | 68 |
| Fineness (% retain on 325 mesh) | 0.01 | 0.01 | 0.02 |
| Brightness (%) | 94 | 91 | 91 |
| Oil Absorption (%) | 55 | 90 | 53 |
| pH (20% solids) | 5.5 | 6.0 | 5.5 |
| Specific Gravity | 2.63 | 2.65 | 2.65 |
| Refractive Index | 1.62 | 1.56 | 1.56 |
| Bulking Value (gallons/pound) | 0.046 | 0.045 | 0.045 |
| Moisture (% maximum) | 0.5 | 0.5 | 0.5 |
| Chemical Analysis (%) | | | |
| Aluminum Oxide | — | 44.48 | 44.48 |
| Silicon Dioxide | — | 52.41 | 52.41 |
| Titanium Dioxide | — | 1.79 | 1.79 |
| Ferric Oxide | — | 0.58 | 0.58 |
| Calcium Oxide | — | 0.03 | 0.03 |
| Magnesium Oxide | — | 0.02 | 0.02 |
| Sodium Oxide | — | 0.28 | 0.28 |
| Potassium Oxide | — | 0.15 | 0.15 |
| Ignition Loss | — | 0.20 | 0.20 |

Especially suitable calcined kaolins include Kaopolite 1147, available from Kaopolite, Inc., and WHITETEX and AL-SIL-ATE S, available from Freeport Kaolin Company. Where desired, mixtures of two or more calcined kaolins in accordance with this invention may be employed.

The talc modifier may be substantially any high quality talc containing low levels of calcium and other elements incompatible with anticariogenic adjuvants. One especially suitable talc is 141 Talc U.S.P., a bacterial controlled talc available from Whittaker, Clark & Daniels, Inc. Another suitable talc is Cercron talc No. MP96-28 available from Pfizer, Inc. Typical properties of useful talcs are given in Table II.

TABLE II

| TALC PROPERTIES | | | |
|---|---|---|---|
| | Sample I | Sample II | Sample III |
| Physical Properties | | | |
| Median Particle Size (micrometers) | 5 | 12 | 8 |
| Particle Size (% <2 micrometers) | 24 | 2 | 17 |
| Fineness (% retain on 325 mesh) | 0 | 17 | 1 |
| Brightness (%) | 89 | 91 | 88 |
| pH (20% solids) | 8.7 | 8.8 | 9.0 |
| Specific gravity | 2.70 | 2.70 | 2.80 |
| Tapped Bulk Density (pounds/cubic foot) | 40 | 59 | 54 |
| Moisture (% maximum) | 0.5 | 0.5 | 0.2 |
| Chemical Analysis | | | |
| Magnesium Oxide | 32 | 30 | 32 |
| Silicon Dioxide | 62 | 61 | 62 |
| Calcium Oxide | 0.2 | 0.09 | 0.5 |
| Aluminum Oxide | 0.6 | 0.9 | 0.5 |
| Ferric Oxide | 1.0 | 0.9 | 1.0 |
| Titanium Dioxide | — | 0.05 | — |
| Sodium Oxide | — | 0.07 | — |
| Potassium Oxide | — | 0.01 | — |
| Ignition Loss | 5.0 | 5.13 | 5.0 |

Whiteness of the abrasive mixture is enhanced by adding a minor amount (i.e., about 2–20%, by weight of the mixture) of titanium dioxide as a whitening agent. Preferably, about 5–15% titanium dioxide, by weight, is present.

The cleaning and polishing mixture of this invention comprises at least about 20% calcined kaolin, at least about 10% talc, and, preferably, about 2–20% titanium dioxide, all by weight of the total cleaning and polishing mixture. It is especially desired that the mixture comprise about 60–80% calcined kaolin, about 5–15% titanium dioxide and balance talc. An especially preferred mixture comprises about 75% calcined kaolin, about 20% talc, and about 5% titanium dioxide.

Exemplary abrasive mixtures in accordance with this invention are set forth in the following examples.

EXAMPLE I

| Abrasive Ingredient | Parts By Weight |
|---|---|
| Calcined Kaolin I | 27.0 |
| Talc I | 7.0 |

EXAMPLE II

| Abrasive Ingredient | Parts By Weight |
|---|---|
| Calcined Kaolin II | 15.0 |
| Talc II | 15.0 |
| Titanium Dioxide | 2.0 |

EXAMPLE III

| Abrasive Ingredient | Parts By Weight |
|---|---|
| Calcined Kaolin I | 22.0 |
| Calcined Kaolin II | 7.0 |
| Talc I | 7.0 |
| Titanium Dioxide | 1.0 |

DENTIFRICE PREPARATIONS

The mixture of cleaning and polishing agents of the present invention is employed in dentifrice preparations within the range of about 10 up to about 95%, by weight, depending upon the particular formulation desired, as is well known to one skilled in the art.

Toothpastes preferably contain a total of about 20–70% cleaning and polishing mixture, by weight, whereas tooth powders contain about 60–90% cleaning and polishing mixture, by weight. Liquid dentifrices typically employ about 10–40%, by weight, abrasive, whereas gel type dentifrices utilize about 20–40% cleaning and polishing mixture, by weight.

Dentifrice preparations utilizing the cleaning and polishing agents of the subject invention are prepared in a conventional manner and usually include additional ingredients which render the overall composition commercially acceptable to consumers.

Thus, toothpastes require a binder substance to impart desired textural properties. Natural gum binders such as xanthan, tragancanth, gum karaya, gum arabic, guar etc. and seaweed derivatives such as carragheen and alginates, and water-soluble cellulose derivatives, such as methyl cellulose, sodium carboxymethyl cellulose, and hydroxyethyl cellulose, can be used for this purpose. Synthetic colloidal magnesium silicate, such as those available under the trademark "Laponite", also may be used and is preferred in gel-type formulations. Desirably, those materials are employed which are most compatible with fluoride and stannous ions. Improvements in texture can also be attained by including an additional material such as colloidal magnesium aluminum silicate (available under the trademark "VEE-GUM") and other smectite clays, fumed silica, or the like. Binders in an amount of from 0.5% to 5.0%, by weight, can be used to form a satisfactory toothpaste.

Toothpastes conventionally contain organic surface-active agents, which may be anionic, cationic, nonionic, or ampholytic in nature. Preferably, the agent possess detergent and foaming properties as well. Suitable sudsing agents include, but are not limited to, water-soluble alkyl sulfates having from 8 to 18 carbon atoms in the alkyl radical, such as sodium lauryl sulfate, water-soluble salts of sulfonated monoglycerides of fatty acids having from 10 to 18 carbon atoms in the alkyl radical such as sodium coconut monoglyceride sulfonate, salts of fatty acid amides of taurines such as sodium-N-methyl palmitoyl taurine, and salts of fatty acid esters of isethionic acid.

Other particularly suitable surface-active materials include nonionic agents such as condensates of sorbitan monostearate and ethylene oxide, copolymers of the poly(oxypropylene)-poly(oxyethylene) type (e.g., Pluronic) and amphoteric agents such as quaternized imidazole derivatives (e.g., Miranol). Useful cationic surface-active germicides and antibacterial compounds include tertiary amines containing one fatty alkyl group and two poly(oxyethylene) groups, benzyl dimethyl stearyl ammonium chloride, and di-isobutylphenoxyethoxyethyl dimethyl benzyl ammonium chloride. Surface-active agents can be used in the compositions of this invention in an amount of from about 0.5% to about 5.0%, by weight, of the total composition.

Cationic antibacterial agents may be included in compositions of the present invention. Such agents among others include quaternary ammonium compounds, such as benzethonium chloride and cetylpyridinium chloride, and biguanides, such as chlorhexidine, alexidine, hexetidine, and polyhexamethylene biguanide hydrochloride (Cosmocil CQ). These agents may be used in effective amounts ranging from about 0.01 to 5 percent by weight of the dentifrice.

It is also desirable to include some humectant material in a toothpaste to keep it from hardening. Materials commonly used for this purpose include glycerin, sorbitol, and other polyhydric alcohols. The humectants can comprise up to 35% of conventional toothpaste compositions. In the case of gel-type formulations, humectants may be used at levels as high as 80%, by weight.

Finally, flavoring materials may be included in a toothpaste formulation including small amounts of oils of spearmint, wintergreen and peppermint or other natural or synthetic flavors and sweetening agents such as saccharin, cyclamate, aspartame, dextrose, and levulose.

The non-fluoride dentifrices of this invention generally are employed at their natural pH values which lie in the range of about 6.0–8.0, although, if desired, the pH may be adjusted in the range of about 4.0–9.0 with carboxylic acids, various sodium phosphates or other buffering agents.

Compositions of exemplary dentifrice preparations employing the cleaning and polishing agents of the present invention are given in the following Examples.

EXAMPLE IV

| Ingredient | Parts By Weight |
|---|---|
| Calcined Kaolin I | 24.00 |
| Calcined Kaolin II | 7.00 |
| Talc I | 7.00 |
| Titanium Dioxide | 1.00 |
| Glycerin | 7.00 |
| Sorbitol (70%) | 24.00 |
| Distilled Water | 24.92 |
| Magnesium Aluminum Silicate | 0.78 |
| Hydroxyethyl Cellulose | 0.75 |
| Trisodium Citrate Dihydrate | 0.25 |
| Sodium Lauryl Sulfate | 1.50 |
| Flavors, Sweeteners, Preservatives, etc. | 1.80 |

EXAMPLE V

| Ingredient | Parts by Weight |
|---|---|
| Calcined Kaolin II | 19.00 |
| Talc II | 19.00 |
| Titanium Dioxide | 2.00 |
| Glycerin | 12.00 |
| Sorbitol (70%) | 12.00 |
| Distilled Water | 31.05 |
| Laponite D | 0.30 |
| Sodium Carboxymethyl Cellulose | 1.55 |
| Sodium Citrate Dihydrate | 0.25 |
| Sodium Lauryl Sulfate | 1.50 |
| Flavors, Sweeteners, Preservatives, etc. | 1.35 |

EXAMPLE VI

| Ingredient | Parts by Weight |
|---|---|
| Calcined Kaolin III | 23.00 |
| Talc III | 12.00 |
| Titanium Dioxide | 5.00 |
| Glycerin | 5.00 |
| Sorbitol (70%) | 23.00 |
| Distilled Water | 27.15 |
| Laponite D | 0.30 |
| Sodium Carboxymethyl Cellulose | 1.35 |
| Sodium Citrate Dihydrate | 0.25 |
| Sodium Lauryl Sulfate | 1.50 |
| Flavors, Sweeteners, Preservatives, etc. | 1.45 |

As previously indicated, the cleaning and polishing agents of the present invention also function as compatible carriers for anticariogenically-effective and non-toxic amounts of water-soluble fluoride-containing anticariogenic adjuvants in anticariogenic dentifrice preparations. Preferably, the adjuvant is present in the form of water-soluble fluoride-containing compounds capable of supplying fluoride. The preferred adjuvant is a 1:2 molar mixture of sodium fluoride, NaF, and stannous fluoride, $SnF_2$, although other materials such as sodium monofluorophosphate, stannous fluorozirconate ($SnZrF_6$), indium fluorozirconate ($InZrF_7$) and complex zirconium-germanium fluorides (e.g. $Zr(GeF_6)_2$, $ZrGeF_8$, $Ge(ZrF_6)_2$, and $ZrOGeF_6$) may be employed. Sodium fluoride and stannous fluoride are preferred by reason of anticariogenic effectiveness obtainable therewith.

Other suitable adjuvants include water-soluble fluoride salts such as $SnF_4$, $KF$, $InF_3$, $PbF_2$, $FeF_2$, $NH_4F$, and $LiF$, as well as more complex water-soluble fluoride-containing adjuvants such as fluorosilicates, e.g., $Na_2SiF_6$, other fluorozirconates, e.g. $CaZrF_6$, $Na_2ZrF_6$, $K_2ZrF_6$, fluorostannites, e.g. $NaSnF_3$, fluoroborates, e.g. $NaBF_4$, fluorotitanates, e.g., $NaTiF_5$, other fluorogermanates, e.g. $K_2GeF_6$, and mixed halides, e.g., $SnClF$ and $Sn_2ClF_3$. Mixtures of suitable adjuvants may also be utilized. Another suitable adjuvant comprises a mixture of a fluoride salt and an active phosphate compound such as Victamide as set forth and described in U.S. Pat. No. 3,666,855, issued May 30, 1972.

In general, an anticariogenic dentifrice preparation produced in accordance with the subject invention will contain from about 0.05 up to 1.0%, by weight of the dentifrice preparation, of the fluoride-containing anticariogenic adjuvant so as to desirably provide about 1000 ppm fluoride ion. Sodium fluoride is preferably provided at a level of 0.22%, by weight, and when $SnF_2$ is utilized, the desired amount is preferably about 0.4%. As noted, it is especially desired to employ a 1:2 molar ratio of sodium fluoride and stannous fluoride.

Preferably, such fluoride-containing dentifrice preparations are employed in their natural pH ranges (i.e., about pH 3 to pH 8, although, if desired, the pH range may be adjusted to about pH 4 to pH 9 with various buffering agents.

Exemplary formulations of fluoride-containing dentifrices in accordance with this invention are given in the following examples.

EXAMPLE VII

| Constituent | Parts By Weight |
| --- | --- |
| Calcined Kaolin I | 22.00 |
| Calcined Kaolin II | 7.00 |
| Talc I | 7.00 |
| Titanium Dioxide | 2.00 |
| Glycerin | 7.00 |
| Sorbitol (70%) | 24.0 |
| Distilled Water | 24.0 |
| Magnesium Aluminum Silicate | 0.78 |
| Hydroxyethyl Cellulose | 0.75 |
| Sodium Lauryl Sulfate | 1.50 |
| Citric Acid | 0.96 |
| Sodium Hydroxide | 0.25 |
| Sodium Fluoride | 0.05 |
| Stannous Fluoride | 0.33 |
| Flavors, Sweeteners, Preservatives, etc. | 2.38 |

EXAMPLE VIII

| Ingredient | Parts by Weight |
| --- | --- |
| Calcined Kaolin (U. S. Pat. No. 4,122,163) | 18.00 |
| Talc III | 18.00 |
| Titanium Dioxide | 4.00 |
| Glycerin | 5.00 |
| Sorbitol (70%) | 23.00 |
| Distilled Water | 27.03 |
| Laponite D | 0.30 |
| Sodium Carboxymethyl Cellulose | 1.35 |
| Sodium Citrate Dihydrate | 0.25 |
| Sodium Lauryl Sulfate | 1.50 |
| Sodium Fluoride | 0.22 |
| Flavors, Sweeteners, Preservatives, etc. | 1.35 |

EXAMPLE IX

| Ingredient | Parts by Weight |
| --- | --- |
| Calcined Kaolin II | 19.00 |
| Talc II | 19.00 |
| Titanium Dioxide | 2.00 |
| Glycerin | 12.00 |
| Sorbitol (70%) | 12.00 |
| Distilled Water | 29.25 |
| Xanthan Gum | 1.55 |
| Sodium Citrate Dihydrate | 0.25 |
| Sodium Lauryl Sulfate | 1.50 |
| Potassium Acid Phthalate | 1.00 |
| Stannous Fluoride | 0.41 |
| Flavors, Sweeteners, Preservatives, etc. | 2.04 |

EXPERIMENTAL EVALUATIONS

The superiority of the purified, calcined kaolin cleaning and polishing compositions disclosed herein has been substantiated by the following experimental evaluations.

1. Enamel Polish Procedure

Enamel polish was determined with specially prepared teeth that were chemically dulled and then polished with a slurry of an abrasive or dentifrice using an automatic toothbrushing machine. The degree of polish was determined with a reflectometer that measured the intensity of specular light reflected by the treated tooth specimens. The greater the intensity of the reflected light from a specimen, the higher was the luster of the tooth and consequently the higher was the numerical polish score. The details of this procedure have been previously described in detail in Putt et al., *J. Dent. Res.* 59:1177 (1980).

2. Cleaning Procedure

The degree of cleaning was assessed by measuring the amount of plastic removed by brushing with abrasive slurries. The amount of plastic removed was quantitated by profilometry. The greater the quantity of plastic removed by the brushing treatment, the deeper was the abraded area, and consequently, the higher was the cleaning score.

All evaluations were made on Plexiglas blocks that were cut and milled from ¼ inch thick sheets into 2-cm squares. Brushing treatments were administered with the V-8 Crossbrushing Machine at a pressure of 300 grams for 2000 strokes. Abrasive slurries were prepared by mixing one part of abrasive by weight with 2 parts of a 1% sodium carboxymethyl cellulose solution.

Surface profile measurements were made with a profilometer. This instrument is a surface topography measurement and analysis system utilizing a diamond stylus with a tip radius of 0.0001 inch. The stylus traces the surface of a specimen and produces an analog signal that is an exact replica of the traced surface topography.

The signal that is produced can be recorded on a strip chart in its original form or modified and analyzed prior to recording. In the analysis of Plexiglas specimens, the high-frequency roughness signals were electronically filtered from the original signal. Cleaning scores were reported in micro-inches as mean depth measurements of the abraded area. The mean depth was determined by dividing the area of the abraded cross section of each profilometer trace by the width of the abraded area. The area of the cross section was measured with a planimeter, providing a quantitative representation of the extent of material loss along the path traced. This value is used as an absolute measure of the ability of the abrasive slurry to remove plastic from the block.

The foregoing laboratory assessment of cleaning correlates well with cleaning observations in human clinical investigations as well as the RDA method of measuring dentin abrasion described below.

3. Dentin Abrasion Procedure

The dentin abrasion procedure measures the relative abrasiveness of a dentifrice compared to a standard material. Quantitative determination of abrasivity was accomplished by brushing radioactive dentin with a suspension of a dentifrice. The amount of dentin abraded was proportional to the abrasiveness of the dentifrice tested and was measured by the level of radioactivity in the suspension after the brushing treatment. The procedure has been described previously in Hefferren, *J. Dent. Res.* 55:563, 1976.

4. Instrumental Method of Measuring Whiteness

Whiteness of dentifrice samples was determined by a procedure similar to TAPPI test method T-646 using a DU Spectrophotometer (Model 2400) with a Diffuse Reflectance Attachment (Model 2580). The diffuse reflectance attachment measures the diffuse reflectance of opaque liquid or solid samples relative to a standard. Radiation from a tungsten lamp is dispersed by a prism and the wavelength is manually set. The monochromatic light strikes the sample surface and diffuse light reflected upward from the sample at angles between 35° and 55° strikes an ellipsoidal mirror, passes through an opal glass diffusing screen to the photodetector. The reflectance observed at 450 nm is representative of the visual whiteness of the sample using magnesium oxide as the reflectance standard.

5. Dentifrice Rheology

The rheology of dentifrice samples was determined by means of a Brookfield Viscometer (Model RVT) equipped with a T-Bar F spindle and a Helipath stand. Dentifrice samples were extruded into a 150 ml beaker and allowed to stand for 24 hours. Viscometer readings were made at eight different rotational speeds at the midpoint of descent and ascent 1.5 cm below the paste surface.

Using the foregoing technique dentifrices and abrasives in accordance with this invention were evaluated as follows. Enamel polish data were obtained using the foregoing technique for water slurries of a series of mixtures of talcs (Table II above) with different kaolins, namely, calcined kaolins I, II and III (Table I above) and the purified calcined kaolin of U.S. Pat. No. 4,122,163. These enamel polish data are provided in Table III. The data show that superior polishing results are achieved with water slurries of all calcined kaolin-talc mixtures containing about 20% or more calcined kaolin. The data also show that talc in fact enhances the polishing ability of many of the mixtures relative to either constituent alone.

TABLE III

ENAMEL POLISH OF WATER SLURRIES OF CALCINED KAOLINS AND TALC

| Ratio of Calcined Kaolin to Talc I | Calcined Kaolin I | Calcined Kaolin II | Calcined Kaolin III | Purified Calcined Kaolin** |
|---|---|---|---|---|
| | Polish Score* | | | |
| 1:0 | 104 ± 1 | 96 ± 1 | 100 ± 2 | 103 ± 2 |
| 4:1 | 110 ± 1 | 99 ± 1 | 106 ± 1 | 111 ± 1 |
| 3:2 | 112 ± 1 | 104 ± 2 | 107 ± 1 | 112 ± 1 |
| 2:3 | 112 ± 1 | 107 ± 1 | 110 ± 1 | 112 ± 2 |
| 1:4 | 91 ± 4 | 94 ± 2 | 108 ± 1 | 108 ± 2 |
| 0:1 | 40 ± 2 | 40 ± 1 | 49 ± 2 | 40 ± 2 |

*Means ± standard error of 6 replicates.
**U. S. Pat. No. 4,122,163.

Table IV reports cleaning scores for various mixtures of calcined kaolin and talc. These data also demonstrate that such mixtures containing at least about 20% calcined kaolin perform extremely well from a cleaning standpoint.

TABLE IV

CLEANING OF MIXTURES OF CALCINED KAOLIN AND TALC

| Ratio Calcined Kaolin III to Talc I | Cleaning Scores (μ in)* |
|---|---|
| 1:0 | 190 ± 11 |
| 4:1 | 173 ± 6 |
| 3:2 | 151 ± 9 |
| 2:3 | 110 ± 11 |
| 1:4 | 88 ± 6 |
| 0:1 | 24 ± 4 |

*Mean ± standard error of 8 replicates.

Cleaning and dentin abrasion scores were obtained using the foregoing procedures for a number of dentifrices incorporating calcined kaolin abrasives, some containing talc. For comparative purposes, scores were also obtained for dentifrices containing other abrasive systems. The data are presented in Table V. In all cases, cleaning performance was not adversely affected by the presence of talc in the calcined kaolin formulations.

In spite of the success of the calcined kaolin-talc mixtures as cleaning and polishing agents, they are not unduly abrasive. The abrasion data of Table V demonstrate the relative safety and low abrasion for the mixtures of this invention. These data indicate that the addition of talc to calcined Kaolin dentifrices decreases abrasivity to dentin without causing appreciable diminution in cleaning ability.

TABLE V

CLEANING AND ABRASION OF CALCINED KAOLIN-TALC DENTIFRICES

| Dentifrice Abrasive System | Cleaning Score* (μ in) | Abrasion Score* |
|---|---|---|
| 36% Calcined Kaolin I | 112 ± 4 | 98 ± 1 |
| 28% Calcined Kaolin I, 6% Calcined Kaolin III | 131 ± 6 | 131 ± 2 |
| 21% Calcined Kaolin I, 6% Calcined Kaolin III, 6% Talc I | 120 ± 6 | 70 ± 3 |
| 21% Calcined Kaolin I, 13% Calcined Kaolin III | 147 ± 8 | 117 ± 3 |
| 14% Calcined Kaolin I, 13% Calcined Kaolin III, 6% Talc I | 133 ± 4 | 98 ± 3 |
| 19% Calcined Kaolin III, 19% Talc II | 131 ± 5 | 94 ± 5 |
| 37% Purified, Calcined Kaolin | 110 ± 3 | 97 ± 4 |

TABLE V-continued
CLEANING AND ABRASION OF CALCINED KAOLIN-TALC DENTIFRICES

| Dentifrice Abrasive System | Cleaning Score* ($\mu$ in) | Abrasion Score* |
|---|---|---|
| (U.S. Pat. No. 4,122,163) | | |
| $CaHPO_4.2H_2O$, $CaCO_3$ | 66 ± 4 | 61 ± 2 |
| $CaCO_3$, $Al(OH)_3$ | 96 ± 7 | 101 ± 4 |

*Mean ± standard error of 8 replicates.

Using the described technique for determining whiteness, the whiteness of a series of dentifrice formulations was measured. The tested dentifrices included calcined kaolin alone, mixtures thereof with talc, and the invention combination of calcined kaolin, talc and titanium dioxide. For comparative purposes, the whiteness of dentifrices based on the highly purified calcined kaolin of U.S. Pat. No. 4,122,163 was also determined. These data, which are reported in Table VI, demonstrate that the degree of whiteness of calcined kaolin-talc dentifrices in combination with titanium dioxide whiteners is equivalent to that of calcined kaolin-dentifrices without talc even though talc has a negative effect on the whiteness of calcined kaolins. Off-color calcined kaolins, such as Calcined Kaolins II and III, may be employed in a dentifrice of acceptable whiteness in accordance with this invention.

TABLE VI
WHITENESS OF CALCINED KAOLIN DENTIFRICES

| Dentifrice Abrasive System | Whiteness (%) |
|---|---|
| 40% Calcined Kaolin II | 72 |
| 38% Calcined Kaolin II, 2% $TiO_2$ | 79 |
| 20% Calcined Kaolin II, 20% Talc I | 68 |
| 19% Calcined Kaolin II, 19% Talc I, 2% $TiO_2$ | 79 |
| 40% Calcined Kaolin III | 69 |
| 38% Calcined Kaolin III, 2% $TiO_2$ | 79 |
| 19% Calcined Kaolin III, 19% Talc II, 2% $TiO_2$ | 79 |
| 40% Purified Calcined Kaolin (U.S. Pat. No. 4,122,163) | 80 |
| 38% Purified Calcined Kaolin, 2% $TiO_2$ | 82 |
| 19% Purified Calcined Kaolin, 19% Talc II, 2% $TiO_2$ | 82 |

Figure 2:
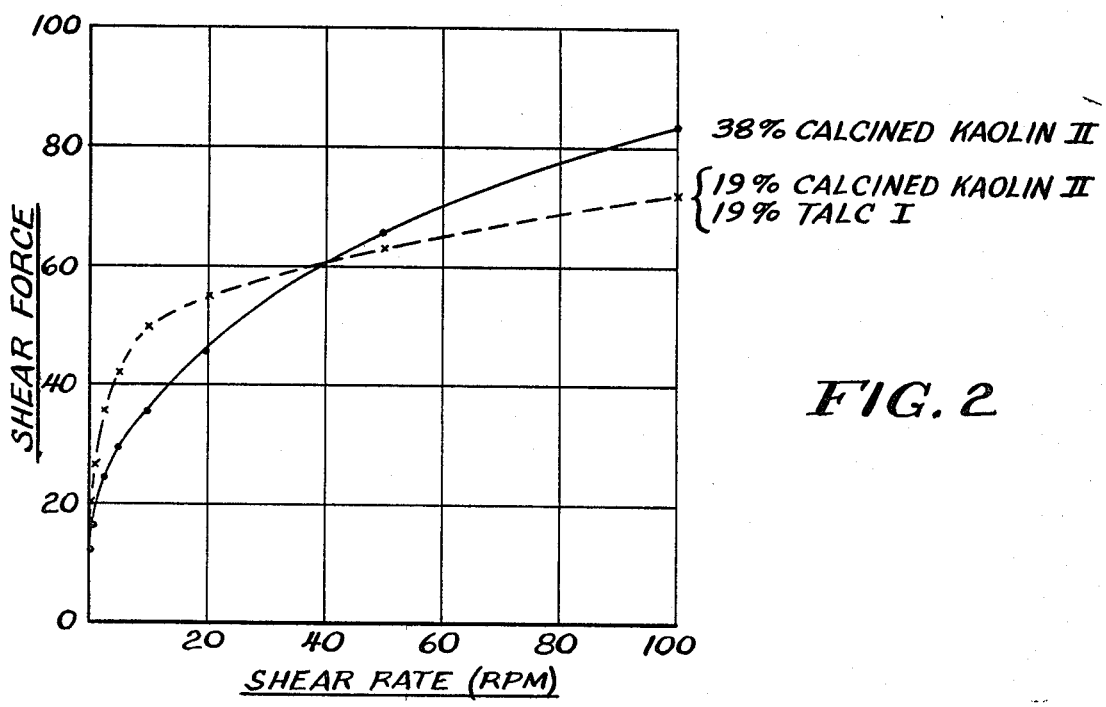
Figure 3:
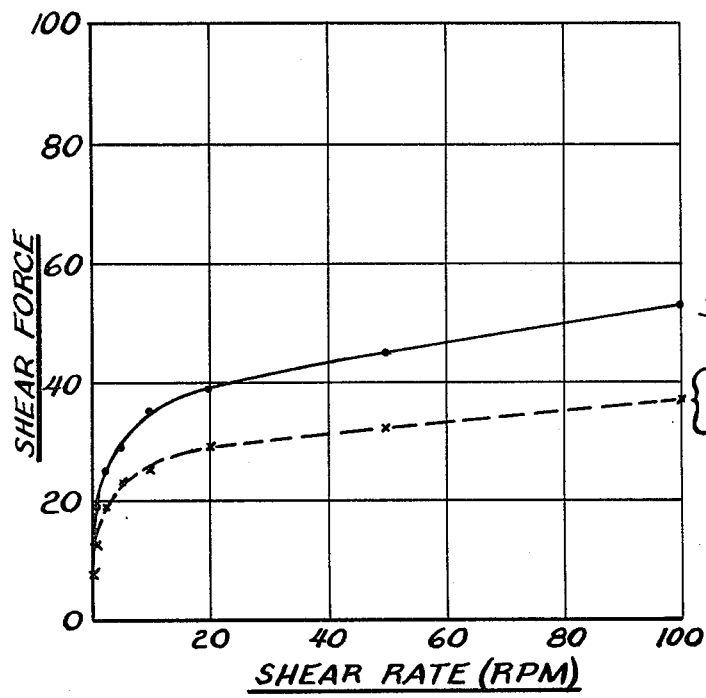
Figure 4:
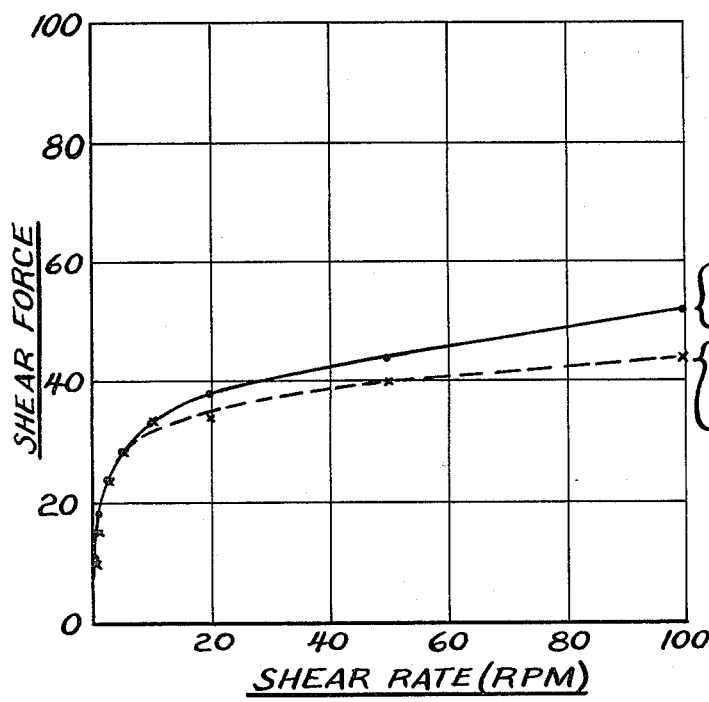

By means of the described technique the rheology of four dentifrice pairs was compared. Each pair of dentifrices included a formulation containing only calcined kaolin as the polishing agent and an identical formulation where a portion of the calcined kaolin was replaced by talc. The data were plotted graphically as shear force (which is proportional to the scale reading) versus shear rate (which is proportional to the speed of rotation) in FIGS. 1-4 of the drawing.

FIGS. 1-4 demonstrate that the addition of talc to dentifrices containing calcined kaolin reduces viscosity slightly and substantially increases shear thinning, a collective term for the combined effects of thixotropy and pseudoplasticity. This reduction in viscosity which occurs at high shear rates with the talc-containing dentifrices results in improved tube filling, extrusion from the tube, and dispersibility during toothbrushing.

In accordance with this invention, it has been discovered that the rheological properties of calcined kaolin-based dentifrices may be remarkably improved by incorporating talc therewith. Further, by employing an additional titanium dioxide additive, the whiteness of off-color calcined kaolin samples may be brought up to acceptable levels.

What is claimed is:

1. In a method for reducing the incidence of dental abrasion caused by regular application to the teeth of a dentifrice preparation comprising as a cleaning and polishing agent calcined kaolin, the improvement consisting of employing therewith at least about 6% talc by weight of the mixture as a modifier.

* * * * *

UNITED STATES PATENT AND TRADEMARK OFFICE
CERTIFICATE OF CORRECTION

PATENT NO. : 4,428,928
DATED : January 31, 1984
INVENTOR(S) : Joseph C. Muhler and Mark S. Putt It is certified that error appears in the above—identified patent and that said Letters Patent is hereby corrected as shown below:

Col. 1, line 45, "peridontal" should be --periodontal--.

Col. 1, line 52, "$(NaPO_3)$," should be --$(NaPO_3)_x$--.

Col. 1, line 68, "es-" should be --aes---.

Col. 2, line 24, "estheti-" should be --aestheti---.

Col. 7, line 26, "agent" should be --agents--.

Col. 9, line 34, "pH8," should be --pH8),--.

Col. 12, line 51, "Kaolin" should be --kaolin--.

Signed and Sealed this

Twelfth Day of June 1984

[SEAL]

Attest:

GERALD J. MOSSINGHOFF

Attesting Officer

Commissioner of Patents and Trademarks